(12) United States Patent
Izumo et al.

(10) Patent No.: US 7,003,404 B2
(45) Date of Patent: Feb. 21, 2006

(54) CONTROL METHOD FOR MOISTURE METER, CONTROL PROGRAM FOR MOISTURE METER, RECORD MEDIUM RECORDING CONTROL PROGRAM FOR MOISTURE METER AND MOISTURE METER

(75) Inventors: Naoto Izumo, Kitamoto (JP); Yuji Fukami, Saitama (JP)

(73) Assignee: A&D Company Limited, Tokyo (JP)

( * ) Notice: Subject to any disclaimer, the term of this patent is extended or adjusted under 35 U.S.C. 154(b) by 0 days.

(21) Appl. No.: 10/653,082

(22) Filed: Sep. 3, 2003

(65) Prior Publication Data

US 2005/0049800 A1    Mar. 3, 2005

(51) Int. Cl.
  *G01N 31/00* (2006.01)
  *G06F 19/00* (2006.01)

(52) U.S. Cl. .................................... 702/30

(58) Field of Classification Search ............... 702/31, 702/127, 19, 22, 108, 99, 130–132, 136; 73/73–77, 25.04, 29.01
See application file for complete search history.

(56) References Cited

U.S. PATENT DOCUMENTS

| | | | | |
|---|---|---|---|---|
| 4,165,633 A * | 8/1979 | Raisanen ........................ 73/76 |
| 4,316,384 A * | 2/1982 | Pommer et al. ................ 73/76 |
| 4,408,482 A * | 10/1983 | Zhuravlev et al. ............. 73/75 |
| 4,750,273 A * | 6/1988 | Parkes et al. ................. 34/484 |
| 4,777,604 A * | 10/1988 | Robinson .................... 700/208 |
| 4,798,252 A | 1/1989 | Knothe et al. |
| 4,845,978 A * | 7/1989 | Whitford ........................ 73/73 |
| 4,889,201 A | 12/1989 | Oldendorf et al. |
| 4,964,734 A * | 10/1990 | Yoshida et al. ............... 374/14 |
| 5,257,532 A * | 11/1993 | Hayakawa et al. ............ 73/75 |
| 5,357,441 A * | 10/1994 | Petty et al. ................. 702/104 |
| 5,983,711 A * | 11/1999 | Pappas et al. ................. 73/76 |
| 6,227,041 B1 * | 5/2001 | Collins et al. ................. 73/76 |
| 6,279,387 B1 * | 8/2001 | Kikuchi ........................ 73/76 |
| 6,463,794 B1 * | 10/2002 | Moshe et al. .................. 73/73 |
| 6,477,888 B1 * | 11/2002 | Mizobe ......................... 73/38 |
| 6,530,160 B1 * | 3/2003 | Gookins ...................... 34/418 |
| 6,747,461 B1 * | 6/2004 | Corak et al. ................ 324/643 |

FOREIGN PATENT DOCUMENTS

| | | |
|---|---|---|
| JP | 59098222 | 6/1984 |
| JP | 2194350 | 7/1990 |
| JP | 6308011 | 11/1994 |

* cited by examiner

*Primary Examiner*—Michael Nghiem
*Assistant Examiner*—Demetrius Pretlow
(74) *Attorney, Agent, or Firm*—Bacon & Thomas, PLLC

(57) ABSTRACT

According to the invention, the heating temperature is sequentially raised gradually to detect a parameter of a time function indicating the change of moisture percentage, and according to the parameter, the optimum heating temperature is calculated. Further, the required mass of a sample is calculated from the measurement accuracy set by an operator and the measurement accuracy of the mass.

11 Claims, 11 Drawing Sheets

FIG. 6

| HEATING TEMPERATURE | TIME t | MEASURED MOISTURE | | | pn OBTAINED FROM MOISTURE PERCENTAGE | px OBTAINED FROM HEATING TEMPERATURE C1, C0 |
|---|---|---|---|---|---|---|
| | | TIME t | TIME t + 30 SEC. | TIME t + 60 SEC. | | |
| 140°C | AFTER 8 MIN | 13.67% | 14.42% | 15.08% | $-4.476 \times 10^{-3}$ | $-4.429 \times 10^{-3}$ |
| 160°C | AFTER 10 MIN | 16.41% | 16.95% | 17.40% | $-5.862 \times 10^{-3}$ | $-5.718 \times 10^{-3}$ |
| 180°C | AFTER 12 MIN | 19.04% | 19.72% | 20.33% | $-4.306 \times 10^{-3}$ | $-7.008 \times 10^{-3}$ |

STARCH OBTAINED FROM POTATOES
(MX-50, SAMPLE: 5g)

| TEMPERATURE | 100°C | 120°C | 140°C | 160°C | 180°C | 200°C |
|---|---|---|---|---|---|---|
| MOISTURE (%) | 9.11 | 13.88 | 15.05 | 15.20 | 15.22 | 15.22 |
| RATE (%/MIN) | 1.33 | 0.54 | 0.07 | 0.00 | 0.01 | 0.00 |
| JUDGMENT | F | E | D | A | C | A |

CORNSTARCH (MX-50, SAMPLE: 5g)

| TEMPERATURE | 100°C | 120°C | 140°C | 160°C | 180°C | 200°C |
|---|---|---|---|---|---|---|
| MOISTURE (%) | 6.87 | 11.10 | 12.51 | 12.79 | 12.88 | 12.93 |
| RATE (%/MIN) | 1.14 | 0.52 | 0.12 | 0.02 | -0.01 | 0.00 |
| JUDGMENT | F | E | D | C | A | B |

SOYBEAN POWDER (MX-50, SAMPLE: 5g)

| TEMPERATURE | 100°C | 120°C | 140°C | 160°C | 180°C | 200°C |
|---|---|---|---|---|---|---|
| MOISTURE (%) | 6.19 | 9.25 | 9.88 | 10.17 | 11.02 | 15.39 |
| RATE (%/MIN) | 1.03 | 0.27 | 0.04 | 0.04 | 0.20 | 1.06 |
| JUDGMENT | E | D | A | A | C | F |

PEANUT BUTTER (PULVERIZED)
(MX-50, SAMPLE: 5g)

| TEMPERATURE | 100°C | 120°C | 140°C | 160°C | 180°C | 200°C |
|---|---|---|---|---|---|---|
| MOISTURE (%) | 1.14 | 1.64 | 2.03 | 2.45 | 3.21 | 5.37 |
| RATE (%/MIN) | 0.11 | 0.07 | 0.06 | 0.07 | 0.17 | 0.44 |
| JUDGMENT | D | B | A | B | E | F |

CONTROL METHOD FOR MOISTURE METER, CONTROL PROGRAM FOR MOISTURE METER, RECORD MEDIUM RECORDING CONTROL PROGRAM FOR MOISTURE METER AND MOISTURE METER

BACKGROUND OF THE INVENTION

This invention relates to a control method for a moisture meter, a control program for a moisture meter, a recording medium recording a control program for a moisture meter and a moisture meter and it is applicable particularly to the heating dry type moisture meter. According to the invention, the heating temperature is sequentially raised gradually to detect a parameter of a time function indicating the change of moisture percentage, and according to the parameter, the optimum heating temperature is calculated, or the required mass of a sample is calculated from the measurement accuracy set by an operator and the measurement accuracy of the mass, whereby a condition for measurement can be set simply and surely.

In the heating dry type moisture meter, the moisture percentage of a sample has been detected by heating moisture to evaporate and measuring the change of mass heretofore. That is, when the mass of the sample before starting such heating (hereinafter referred to as mass before drying) is taken as W, and the mass of the sample after drying is taken as D, the moisture percentage WP of the sample can be expressed by the following formula.

[Formula 1]

$$WP = \frac{W-D}{W} \times 100 \, [\%] \qquad (1)$$

Thus, in the heating dry type moisture meter, when the quantity of a sample is large, the measurement accuracy is improved for that, but it takes much time for drying, resulting in lengthening the measurement time. Therefore, in the conventional moisture meter, when the required accuracy is taken as X[%] and the measurement accuracy of weight in the moisture meter is taken as M[g], the calculation on N=M/X is performed by an operator to find the mass N of the sample. According to this, the measurement accuracy of weight is 1 [mg], and in the case of calculating the moisture percentage with the accuracy of 0.01%, the quantity of the sample is 10 [g].

In the heating dry type moisture meter, when the heating temperature is elevated, moisture can be evaporated in a short time, whereby the time required for measurement can be reduced. When the heating temperature becomes high, however, liquid (e.g. volatile oil or the like) other than moisture contained in the sample volatilizes and decomposes, and when the temperature becomes further higher, an organic matter contained in the sample is carbonized to thereby deteriorate the measurement accuracy.

Thus, in the conventional moisture meter, heating conditions are set by a preliminary test in advance. Here the heating conditions are the time for drying a sample by heating (the heating time), the heating temperature, the elapsed time from the start of heating until the temperature is raised to the heating temperature (the temperature rising time), and the like.

That is, in the preliminary test, a sample is heated at a fixed temperature for a predetermined time, and it is detected whether the mass of the sample is changed by evaporation of moisture or not. The heating in the preliminary test is performed at a temperature of 120° C. or the like for ten minutes. In the case where the mass of the sample continues to change even in heating at such a fixed temperature for a fixed time, the heating temperature is varied until finally the mass of the sample is not changed, or at the heating temperature, the heating time is prolonged.

In the preliminary test, a plurality of samples are prepared, the heating temperature, the heating time and the temperature rising time are variously changed to dry the samples, and according to the test results, the heating conditions determined to be suitable are set.

That is, in the moisture percentage measurement using the conventional moisture meter, the thus obtained heating conditions are set on the moisture meter, and then a quantity of sample, which is found by the calculation, is placed. After that, when the measurement is started, in the moisture meter, the mass of the sample before drying is detected and recorded, and heating for the sample is started on the conditions set by a user. After that, the mass in the course of drying is monitored, and according to the monitoring result, the result of measurement still in progress on the moisture percentage is displayed by arithmetic processing of the formula (1). When the heating time elapses, heating is ended, and the measurement result is displayed.

In thus setting the heating conditions through the preliminary test, however, there is a problem that the conditions can't be set simply and surely.

That is, as described above, in the preliminary test, it is necessary to prepare a plurality of samples and heat the same repeatedly, resulting in the problem that it takes long time to make a measurement.

Sometimes even a volatile constituent is evaporated so that the mass of the sample is not changed, and there is the fear that such a case is mistaken as the case where the mass of the sample is not changed due to evaporation of moisture to set the heating conditions. It is considered that the thus set conditions are not suitable. By the way, in the conventional heating dry meter, it requires skill to set the heating conditions.

As described above, it requires a long time to measure each of the plurality of samples, so in the plurality of samples, it is necessary to keep the moisture percentage from being changed for a long time by preventing evaporation of moisture until the measurement is started. Accordingly, in order to maintain and manage such moisture percentage, the maintenance of measurement environment becomes large-scale. Further, the preliminary test becomes complicated, and the complicated work is one main cause of wrong measurement of moisture percentage.

SUMMARY OF THE INVENTION

The invention is made in consideration of the above points, and it proposes a moisture meter, a control method for a moisture meter, a control program for a moisture meter and a record medium recording the control program for the moisture meter, which may set conditions of measurement simply and surely.

In order to solve the problem, the invention of aspect 1, which is applied to the control method for a moisture meter, includes a moisture percentage detection step of sequentially raising the heating temperature gradually and heating a sample for a preliminary test to detect the change of moisture percentage, a parameter detection step of detecting a parameter of a time function indicating the change of the moisture percentage according to the change of moisture percentage detected in the moisture percentage detection step, and a temperature select step of selecting the temperature suitable for heating the sample according to the parameter.

According to the invention of aspect 2, in the constitution of aspect 1, in the temperature select step, the temperature suitable for heating is selected according to the change of the parameter between the heating temperatures sequentially raised gradually.

According to the invention of aspect 3, in the constitution of aspect 1 or aspect 2, in the temperature select step, a parameter detected at the subsequent heating temperature is calculated by a parameter detected at the heating temperature immediately before, and the immediately preceding heating temperature is selected to be suitable for heating by comparison between the calculated parameter and a parameter based on the measured value.

According to the invention of aspect 4, in the constitution of aspect 1, 2 or 3, the control method includes a heating time calculation step of calculating the time required for heating by the parameter based on the temperature suitable for heating.

According to the invention of aspect 5, in the constitution of aspect 4, in the heating time calculation step, on the basis of the measurement accuracy set by an operator, the time function based on the parameter is calculated, thereby calculating the time required for heating.

According to the invention of aspect 6, in the constitution of aspect 1, 2, 3, 4 or 5, the time function is natural logarithm.

In the invention of aspect 7, it is applied to the control method for a moisture meter, and the method includes a mass calculation step of calculating the required mass of a sample from the measurement accuracy set by an operator and the measurement accuracy of mass of the sample.

According to the invention of aspect 8, in the constitution of aspect 1, 2, 3, 4, 5, 6 or 7, the method includes a step of informing an operator of the processing result.

According to the invention of aspect 9, the invention is applied to a control program for a moisture meter, and the control program is for use in the control method for the moisture meter as in aspect 1, 2, 3, 4, 5, 6, 7 or 8.

According to the invention of aspect 10, the invention is applied to a record medium recording a control program, and the record medium records the control program of aspect 9.

According to the invention of aspect 11, the invention is applied to a moisture meter, and a condition provided for measurement is calculated by the control method for the moisture meter as in aspect 1, 2, 3, 4, 5, 6 or 7.

According to the invention of aspect 12, in the constitution of aspect 11, the moisture meter includes informing means for informing an operator of the processing result.

According to the constitution of aspect 1, the control method has the moisture percentage detection step of sequentially raising the heating temperature gradually and heating a sample for a preliminary test to detect the change of moisture percentage, the parameter detection step of detecting a parameter of a time function indicating the change of the moisture percentage according to the change of moisture percentage detected in the moisture percentage detection step, and the temperature select step of selecting the temperature suitable for heating the sample according to the parameter, whereby it can be detected from the determination on the parameter whether the transition of the heating state from the moisture evaporation step to the next step occurs or not, so that the heating temperature can be selected suitably and in a short time by the use of one sample for a preliminary test. The conditions for the measurement can be set simply and surely.

According to the constitution of aspect 2, in the constitution of aspect 1, the temperature select step, the temperature suitable for heating is selected according to the change of the parameter between the heating temperatures sequentially raised gradually, whereby it can be simply and surely detected whether the transition of the heating stage from the moisture evaporation stage to the next stage occurs or not.

According to the constitution of aspect 3, in the constitution of aspect 1 or 2, in the temperature select step, a parameter detected at the subsequent heating temperature is calculated by a parameter detected at the heating temperature immediately before, and the immediately preceding heating temperature is selected to be suitable for heating by comparison between the calculated parameter and a parameter based on the measured value, whereby the heating temperature can be set to the temperature immediately before the transition of the heating stage from the moisture evaporation stage to the next stage.

According to the constitution of aspect 4, in the constitution of aspect 1, 2 or 3, the control method has the heating time calculation step of calculating the time required for heating by the parameter based on the temperature suitable for heating, whereby the parameter used for setting the heating temperature can be effectively used to find the heating time, so that the conditions for the measurement can be more simply and surely set.

According to the constitution of aspect 5, in the constitution of aspect 4, in the heating time calculation step, on the basis of the measurement accuracy set by an operator, the time function based on the parameter is calculated, thereby calculating the time required for heating, so that the heating time that is enough to satisfy the measurement accuracy can be found.

According to the constitution of aspect 6, in the constitution of aspect 1, 2, 3, 4 or 5, the time function is a natural logarithm, so that the heating temperature, the heating time and the like can be found by approximating the change of moisture percentage due to heating with satisfactory accuracy.

According to the constitution of aspect 7, the method has the mass calculation step of calculating the required mass of a sample from the measurement accuracy set by an operator and the measurement accuracy of a mass of the sample, whereby the mass of the sample, which is enough to satisfy the measurement accuracy and can be measured in a short time, can be simply and surely detected so as to simply and surely set the conditions of measurement.

According to the constitution of aspect 8, in the constitution of aspect 1, 2, 3, 4, 5, 6 or 7, the method has the step of informing an operator of the processing result, whereby the thus selected measurement condition can be relayed to the operator so as to assist the operator's setting of the measurement condition.

Thus, according to the constitution of aspect 9, it is possible to provide a control program for a moisture meter, which may set the conditions of the measurement simply and surely.

According to the constitution of aspect 10, it is possible to provide the record medium recording the control program for the moisture meter capable of setting the conditions of measurement simply and surely.

Further, according to the constitution of aspect 11 or 12, it is possible to provide the moisture meter capable of setting the conditions of measurement simply and surely.

BRIEF DESCRIPTION OF THE DRAWINGS

FIG. 6 is a chart showing the parameters p of measurement result and calculation by contrast with FIG. 4;

DETAILED DESCRIPTION OF THE PREFERRED EMBODIMENTS

The modes for carrying out the invention will now be described in detail with reference to the proper attached drawings.

(1) Constitution of the Mode for Carrying out the Invention

Figure 2:
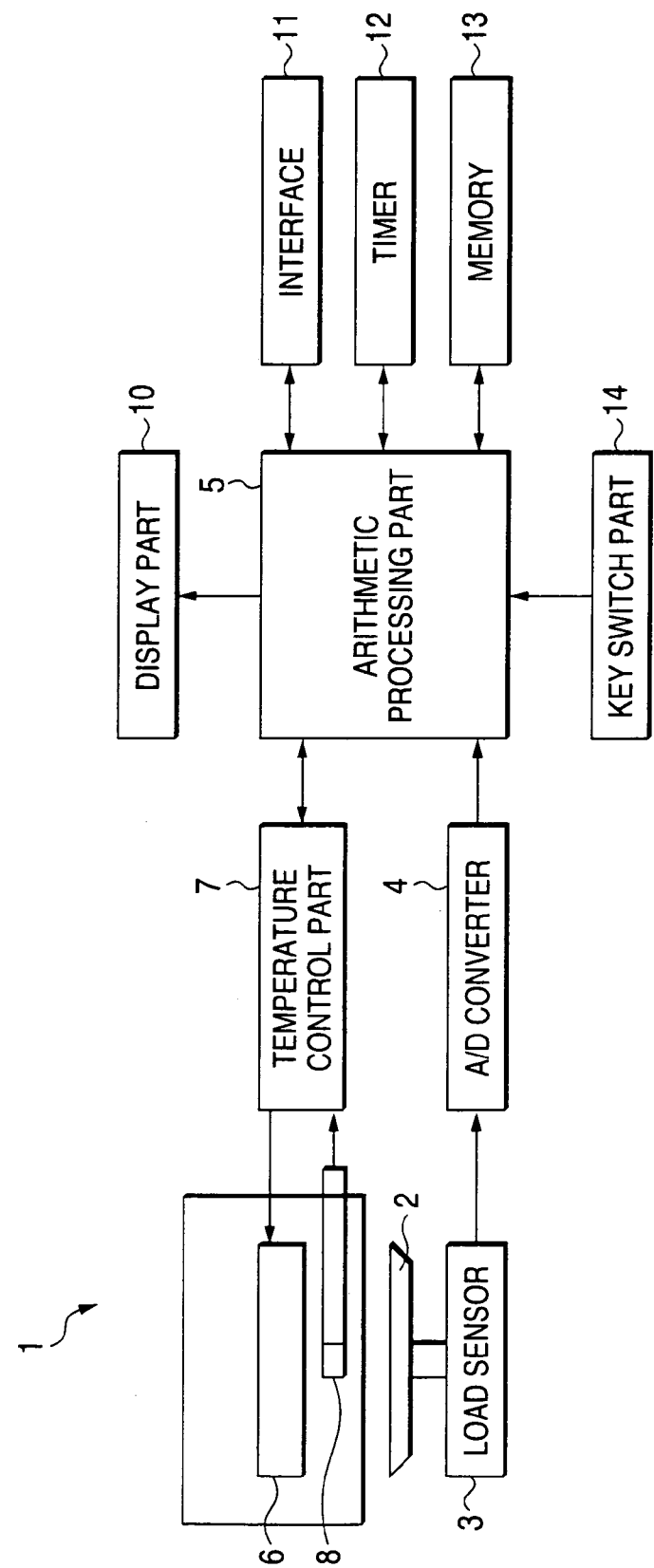
FIG. 2 is a block diagram showing a moisture meter of the arithmetic processing part of FIG. 1.

FIG. 2 is a block diagram showing a moisture meter according to the mode for carrying out the invention. In a moisture meter 1, a sample pan 2 is removably held to place a sample. A load sensor 3 outputs a load detection signal, the signal level of which varies according to the load of the sample pan 2. An analog-to-digital converter (A/D) 4 converts the load detection signal, and the load detection data is output to an arithmetic processing part 5. Thus, the arithmetic processing part 5 is adapted to detect the mass of a sample placed on the sample pan 2 and further the change of the mass.

A halogen lamp 6 is a heat source for heating a sample, and driven by a temperature control part 7 to radiate light for heating the sample. A temperature sensor 8 is disposed in the vicinity of the sample pan 2, and outputs a temperature detection signal, the signal level of which varies according to the temperature. The temperature control part 7 drives the heating lamp 6 while monitoring the heating result according to a temperature detection signal so that the temperature of the sample reaches a temperature designated by the arithmetic processing part 5.

A display part 10 is formed by a liquid crystal display panel or the like to display a users various settings and measurement results. An interface 11 outputs the measurement results and the like to an external device such as a personal computer according to the control of the arithmetic processing part 5 and also outputs data of various settings in the external device to the arithmetic processing part 5. A timer 12 counts the current time, and outputs the count result to the arithmetic processing part 5. A memory 13 constitutes a work area of the arithmetic part 5 and records the measurement results and the like. A key switch part 14 is formed by a pressing operating element required for the operation of the moisture meter 1 to thereby relay various operations of the user to the arithmetic processing part 5.

The arithmetic processing part 5 is a computer for controlling the operation of the whole moisture meter 1, and performs the processing such as preliminary tests and actual measurements according to the operation of the user via the key switch part 14 and the control of the external device.

Figure 1:
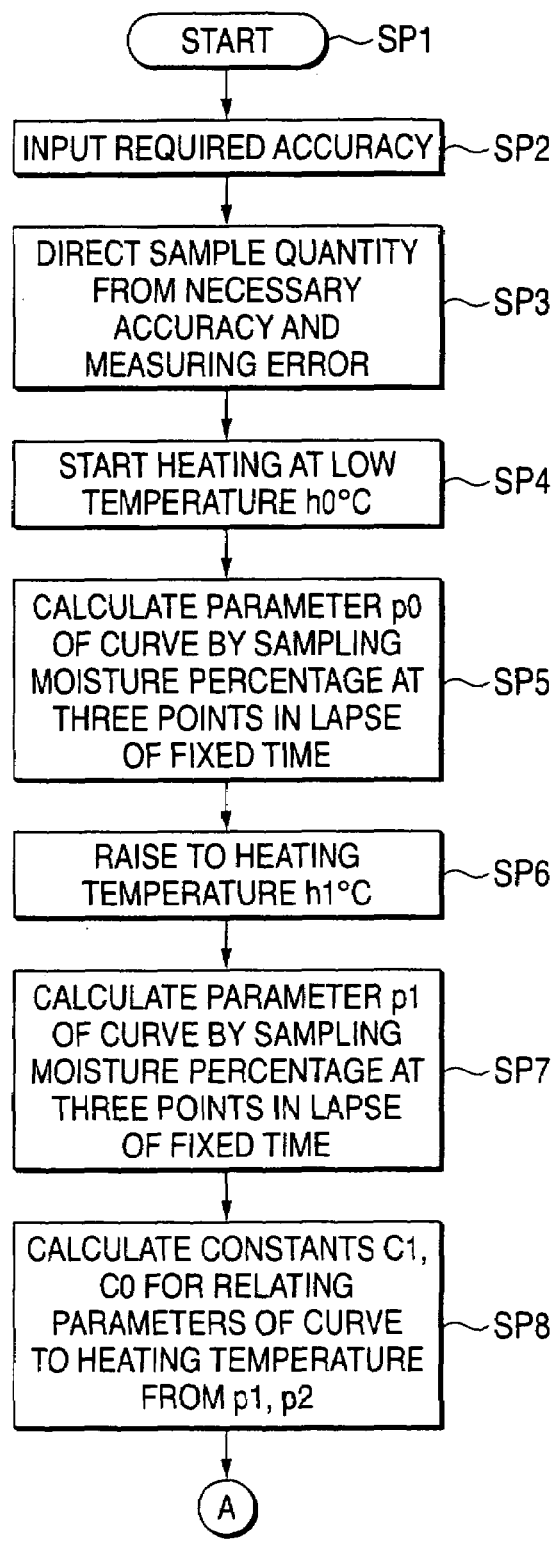
FIG. 1 is a flowchart showing the procedure of an arithmetic processing part in a moisture meter according to the mode for carrying out the invention.

The arithmetic processing part 5 performs the procedure shown in FIG. 1 in the processing of the preliminary tests, thereby instructing the heating condition provided for the actual measurement, the weight of the sample and the like to the user. That is, when the user designates the start of the preliminary test, the transition from the step SP1 to the step SP2 occurs in the arithmetic processing part 5, and the arithmetic processing part displays a settable measurement accuracy on the display part 10, and receives the input of measurement accuracy by detecting the operation of the key switch part 14 corresponding to the display.

Subsequently, in the arithmetic processing part 5, the transition to the step SP3 occurs, and it performs arithmetic processing which has been calculated heretofore by an operator from the measurement accuracy of moisture percentage input by the user to thereby calculate the required mass of the sample and display the same on the display part 10. Thus, the arithmetic processing part 5 determines the necessary mass of the sample.

Subsequently, in the arithmetic processing part 5, the transition to the step SP4 occurs to start heating the sample at a reference temperature of h0 degrees (e.g. 100 degrees) on low temperature side under the control of the temperature control part 7. Further, the arithmetic processing part 5 stores the heating start time, and then causes the transition to the step SP4 to be on standby for the lapse of designated time after the start of heating and measure the moisture percentage. In this measurement, after the lapse of time enough that the temperature of the sample rises after the start of heating, measurement is performed at the different times at least three times in total, and the moisture percentage is calculated at each measurement time.

When the moisture is thus measured, the arithmetic processing part 5 calculates a parameter p0 of a change curve of moisture percentage using the measurement results of moisture percentage of three times measurements. That is, the moisture percentage WP in the lapse of t seconds after the start of heating is expressed by the time function of the following formula.

[Formula 2]

$$WP(t) = \frac{W - D(t)}{W} \times 100 \, [\%] \quad (2)$$

Figure 3:
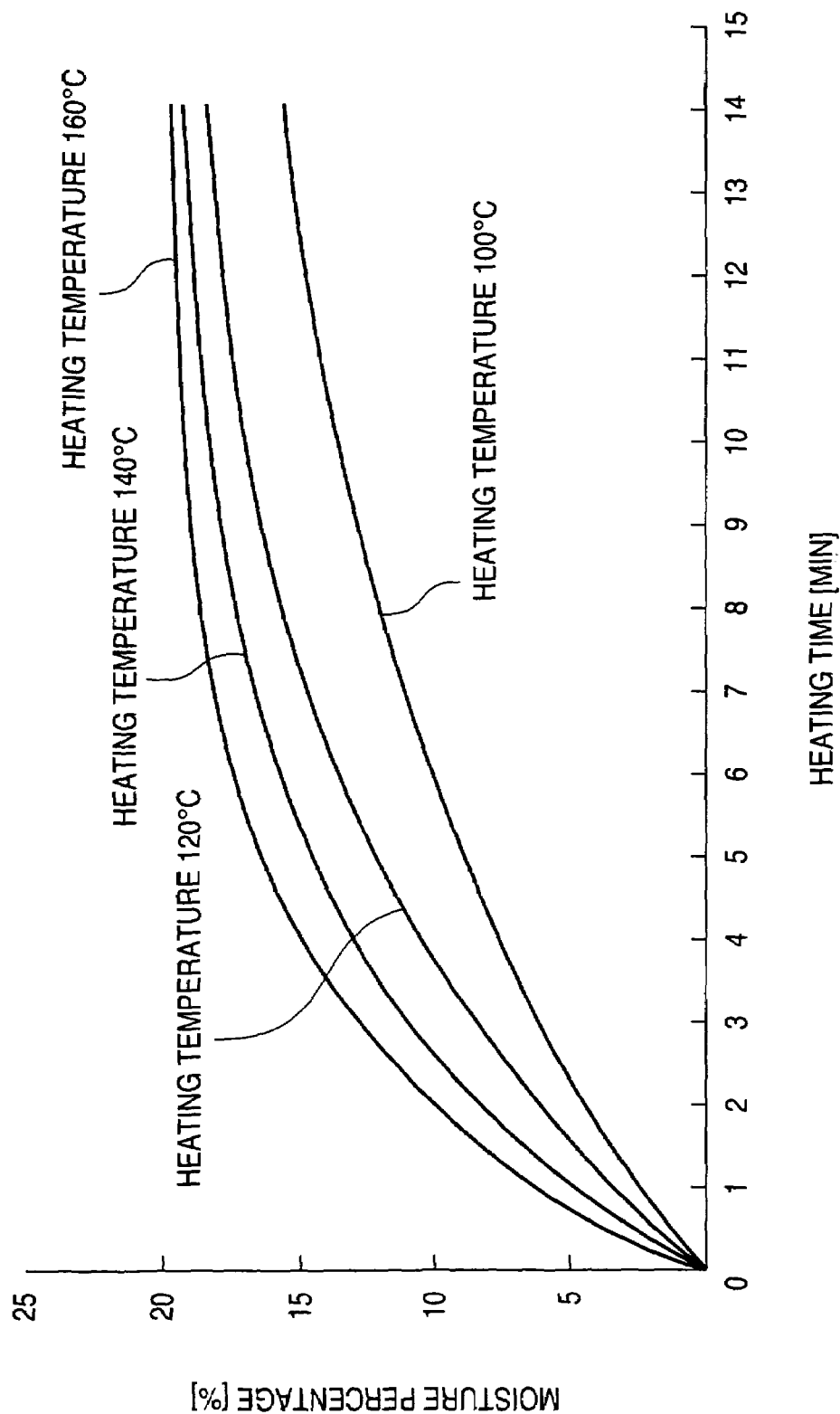
FIG. 3 is a characteristic curve showing the change of moisture percentage depending on each heating temperature.

In the case of heating at a fixed temperature, the change of the moisture percentage can be, as shown in FIG. 3, modeled by a natural logarithm curve, and the moisture percentage WP(t) can be expressed by the following general formula.

[Formula 3]

$$WP(t) = WP \times (1 - e^{K(t)}) \quad (3)$$

WP is the moisture percentage after drying, and K(t) is a parameter of the moisture percentage change curve which is the time function and can be expressed in the natural logarithm curve by the following polynominal using the lapse time t (sec.) after the start of heating, wherein An to A1 are constants.

[Formula 4]

$$K(t) = An \times t^n + An-1 \times t^{n-1} + \ldots + A2 \times t^2 + A1 \times t \quad (4)$$

This polynominal can be approximated with sufficient accuracy by the linear expression shown in the following formula.

[Formula 5]

$$K(t) \approx A1 \times t \quad (5)$$

In the natural logarithm curve expressed taking the heating time as a variable, supposing that substances other than moisture are not evaporated and resolved, it can be expressed taking the heating temperature as a variable. Therefore, if consideration is given to the condition of heating temperature into account, the formula (4) can be expressed by the following formula, wherein h is a heating temperature, and Bn to B0 are constants.

[Formula 6]

$$K(t) = (An \times t^n + An-1 \times t^{n-1} + \ldots + A2 \times t^2 + A1 \times t) \times (Bn \times h^n + Bn-1 \times h^{n-1} + \ldots + B2 \times h^2 + B1 \times h + B0) \quad (6)$$

In here, since the respective series constituting the right-hand side of the formula (6) can be approximated by the linear expression, the formula (6) can be expressed by the following formula, wherein C1 and C0 are constants.

[Formula 7]

$$\begin{aligned}
K(t) &\approx (A1 \times t) \times (B1 \times h + B0) \quad (7)\\
&= (A1 \times B1 \times h + A1 \times B0) \times t\\
&= (C1 \times h + C0) \times t\\
&= p \times t
\end{aligned}$$

When these are summarized, the formula (3) can be expressed by the following formula.

[Formula 8]

$$WP(t) = WP \times (1 - e^{p \times t}) \quad p = C1 \times h + C0 \quad (8)$$

The arithmetic processing part 5 calculates the variable p expressed by the formula (8) by the processing of the step SP5. Further, the arithmetic processing part 5 records the calculation result with the heating temperature in the memory 13. In this operation, the timing of measuring the moisture percentage in the step SP5 is set so that when the arithmetic processing part 5 thus obtains the change of the moisture percentage by approximating the natural logarithm curve, the approximation can be performed with enough accuracy.

To be concrete, when both sides of the formula (8) are differentiated by the time t, the following relational expression can be given.

[Formula 9]

$$\frac{dWP(t)}{dt} = -WP \times p \times e^{p \times t} \quad (9)$$

When the formula (9) is arranged, the following relational expression can be given.

$$e^{p \times t} = -\frac{1}{WP \times p} \times \frac{dWP(t)}{dt} \quad (10)$$

When this relational expression is substituted in the formula (8), the following relational expression can be given.

[Formula 11]

$$\begin{aligned}
WP(t) &= WP \times \left(1 + \frac{1}{WP \times p} \times \frac{dWP(t)}{dt}\right) \quad (11)\\
&= WP + \frac{1}{p} \times \frac{dWP(t)}{dt}
\end{aligned}$$

Further, this formula (11) is arranged, the following relational expression can be given.

[Formula 12]

$$\begin{aligned}
WP &= WP(t) - \frac{1}{p} \times \frac{dWP(t)}{dt} \quad (12)\\
&= WP(t) - \frac{1}{p} \times \frac{WP(t) - WP(t - \Delta t)}{\Delta t}
\end{aligned}$$

In the formula (12), the moisture percentage WP after drying and the parameter p are both unknown numbers, so the parameter p can be calculated by solving the simultaneous equation (12) using the results of at least three times measurements of moisture percentage. Thus, the arithmetic processing part 5 calculates the parameter p by solving the formula (12) about the parameter p using the moisture percentage WP(t) given by three times measurements of moisture percentage in the processing of the step SP5.

Figure 4:
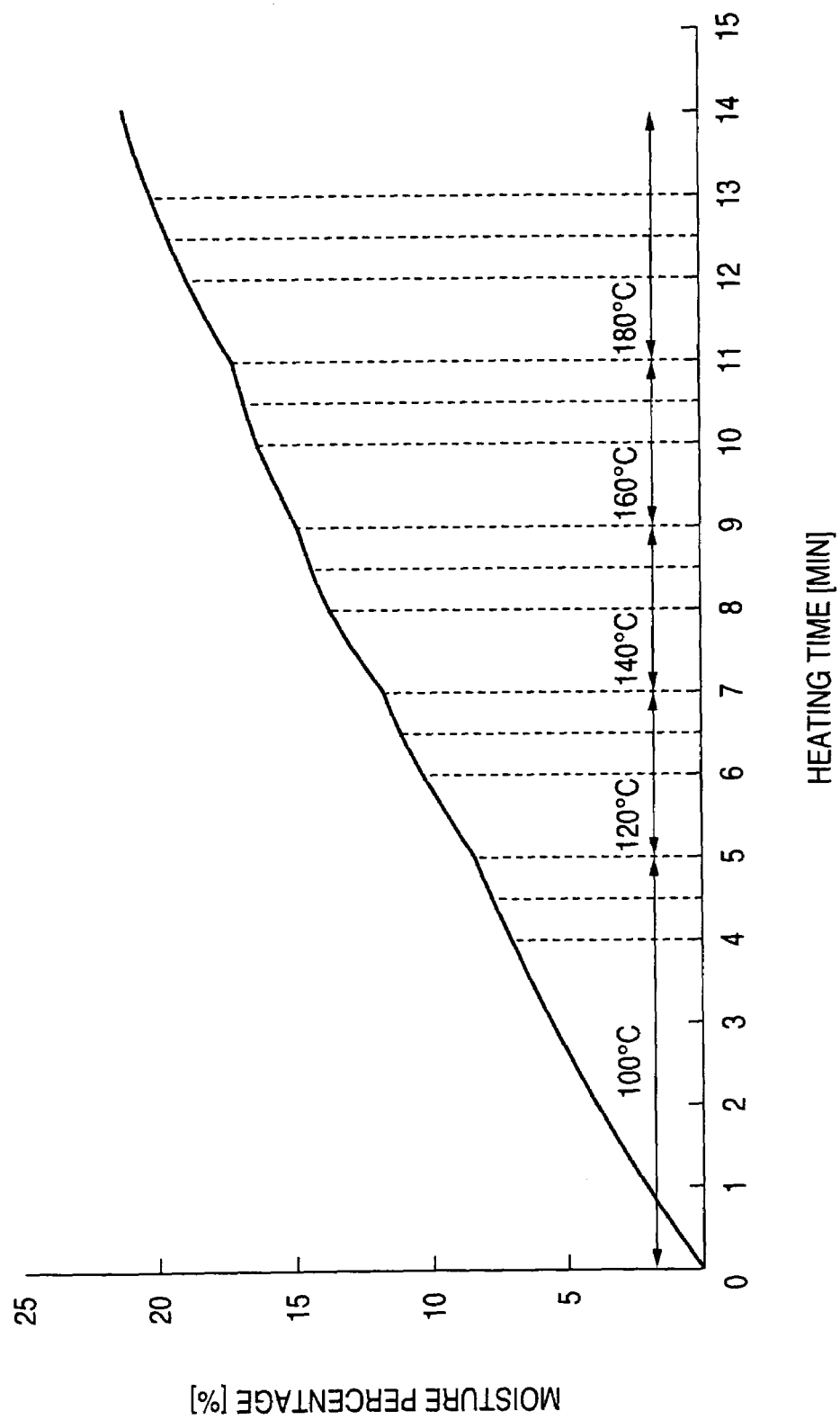
FIG. 4 is a characteristic curve showing the change of moisture percentage in the case of raising the heating temperature gradually.

That is, in the case where a change of moisture percentage as shown in FIG. 4 is observed, when the moisture percentage is calculated in the lapse of four minutes, four minutes and thirty seconds, and five minutes, respectively, and these moisture percentages are 7.02[%], 7.70[%] and 8.35[%], the simultaneous equation shown by the following expression can be given.

[Formula 13]

$$\begin{aligned}
WP &= 7.70 + \frac{1}{p0} \times \frac{7.70 - 7.02}{30} \quad (13)\\
WP &= 8.35 + \frac{1}{p0} \times \frac{8.35 - 7.70}{30}
\end{aligned}$$

Thus, in this case, the parameter p based on $p0 = -1.849 \times 10^{-3}$ can be given by solving the relational expression.

When the parameter p0 is thus obtained by the initial heating temperature h0, in the arithmetic processing part 5, the transition to the step SP6 occurs, the heating temperature is raised by a designated temperature to start to heat the sample at the heating temperature h1 (e.g. 120 degrees). Further in the subsequent step SP7, similarly to the step SP5, a parameter p1 is calculated.

Subsequently, in the arithmetic processing part 5, the transition to the step SP8 occurs to calculate constants C1, C0 of the formula (8) from two of the thus calculated parameters p0 and p1. In here, in this calculation, the constants can be given by solving two simultaneous equations with the parameters p0 and p1. That is, as shown in FIG. 4, heating is started at the subsequent heating temperature h1, the moisture percentage is calculated in the lapse of 6 minutes, 6 minutes and thirty seconds and seven minutes after the first heating start point, respectively, and when these moisture percentages are 10.26%, 11.10%, and 11.87%, the same simultaneous equation as the formula (13) can be given. $P1=-3.139\times10^{-3}$ can be given by solving the equation.

Thus, when $p0=-1.849\times10^{-3}$ and $P1=-3.139\times10^{-3}$ are substituted in the formula (8), the following simultaneous equation can be given.

[Formula 14]

$$-1.849\times10^{-3}=C1\times100+C0 \ -3.139\times10^{-3}=C1\times120+C0 \quad (14)$$

Figure 5:
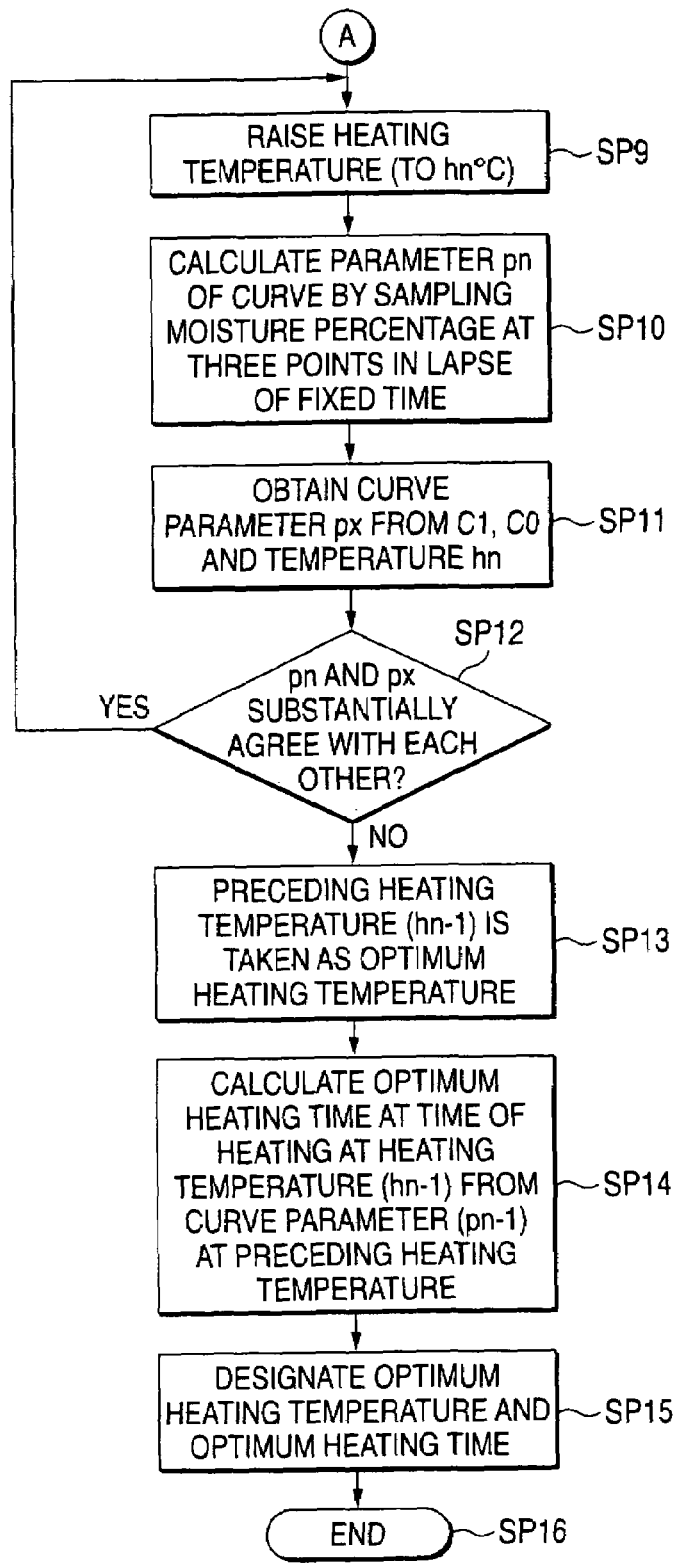
FIG. 5 is a flowchart showing the continuation of FIG. 1.

Thus, $C1=-64.5\times10^{-6}$ and $C1=4.6\times10^{-3}$ can be given by solving the simultaneous equation. When the constants C1 and C0 are thus calculated, in the arithmetic processing part 5, the transition to the step SP9 (FIG. 5) occurs to further raise the temperature by a designated temperature and set the heating temperature to hn.

Further, in the arithmetic processing part 5, the transition to the step SP10 occurs to calculate a parameter pn similarly to the step SP5.

Subsequently, in the arithmetic processing part 5, the transition to the step SP11 occurs to calculate a parameter px at the heating temperature hn from the constants C1, C0 calculated in the step SP8 by the formula (8). Further, in the arithmetic processing part 5, subsequently the transition to the step SP12 occurs to determine whether the parameter px calculated in the step SP11 substantially conforms to the parameter pn calculated from the moisture percentage in the step SP10 or not. According to the determination, the arithmetic processing part 5 determines whether the transition of the heating stage from the stage of drying moisture to the next stage occurs or not.

That is, in a test object provided for this type of test, when the heating temperature is low, an ingredient (a low-volatile ingredient) evaporated at a lower temperature than water such as alcohol is evaporated, and subsequently when the heating temperature is raised, moisture is evaporated. When the heating temperature is further raised, an additive of resin, oil of the sample and the like (high volatile ingredients) are evaporated, and when the temperature is further raised, decomposition and dissolution of organic matter are caused, and further the organic ingredient starts to be carbonized.

Thus, a distinction of change in mass of this type of a sample can be made between the stage of evaporating moisture and the stage other than the moisture evaporation stage by the heating temperature, and in the case of accurately measuring the moisture percentage in the moisture meter, it is necessary to make a measurement with the heating temperature kept at the stage of moisture evaporation. In order to reduce the measurement time, it is necessary that the heating temperature is at the stage of moisture evaporation and the sample is heated at a temperature set as high as possible.

In the case of expressing the change of moisture percentage by the above time function, at the evaporation stage of moisture, in the parameters C1 and C0 of time function detected by the result of measuring the moisture percentage, substantially the coincidence is found at each heating temperature. On the contrary, when the transition of heating stage from the moisture evaporation stage to another stage occurs, for example, oil even other than moisture starts to evaporate, resulting in that the result of measuring the change of the moisture percentage can't be expressed by the time function at the moisture evaporation stage. That is, in this case, the constants C1 and C0 expressing the measurement result by the time function as described above are values different from the constant of the stage until then.

Thus, in the present mode of carrying out the invention, in the step SP12, the parameter Px estimated by the constants C1 and C0 detected by the measurements until then and the parameter Pn by the observation are compared to determine whether the transition of the heating stage to the next stage occurs or not.

In the step SP12, when the comparison result that two kinds of parameters Px and Pn substantially agree with each other is obtained, in this case, sometimes it is considered that a margin of raising the heating temperature is still allowed at the stage of moisture evaporation, so in the arithmetic processing part 5, the transition to the step SP9 occurs to further raise the temperature.

Thus, the arithmetic processing part 5 repeats the procedure of the step SP9–SP10–SP11–SP12–SP9 to sequentially raise the heating temperature until the transition of the heating stage from the moisture evaporation stage to the next stage occurs.

FIG. 6 is a chart showing the actual measurement results in the case of thus raising the temperature. In this case, when the heating temperature is set to 180 degrees, two kinds of parameters Px and Pn are clearly different values, from which it is known that the transition of the heating temperature to the next stage occurs.

Thus, when the transition of the heating stage from the moisture evaporation stage to the next stage occurs, the negative result is given in the step SP12, so the transition from the step SP12 to the step SP13 occurs in the arithmetic processing part 5. In this case, the current heating is in the state of transition from the moisture evaporation stage to the next stage, and also this immediately preceding heating state is determined to be the moisture evaporation stage, so the arithmetic processing part 5 sets the immediately preceding heating temperature to the optimum heating temperature.

Subsequently, in the arithmetic processing part 5, the transition to the step SP14 occurs to substitute the parameter Pn−1 detected at the optimum heating temperature in the formula (8), thereby calculating the optimum heating time which will satisfy the necessary accuracy input in the step SP2. That is, in the present mode for carrying out the invention, in the calculation using the formula (8), the time when the moisture percentage is equal to or lower than the measurement accuracy designated by the user for the final value of the moisture percentage is set to the end time of heating. That is, in this case, when the operator designates the measurement accuracy of 0.2 [%] as the necessary accuracy, for example, the following arithmetic expression can be given by the formula (8).

[Formula 15]

$$\frac{WP(t)}{WP} = (1 - e^{p\times t}) \quad (15)$$

$$= (1 - 0.002)$$

[Formula 16]

$$e^{pxt} = 0.002 \quad (16)$$

[Formula 17]

$$t = \frac{ln(0.002)}{p} \quad (17)$$

When the value $-5.862 \times 10^{-3}$ of the parameter p detected at the temperature of 160 degrees in FIG. 6 is substituted in the formula (17) to solve the equation, the time required for heating, t=1068 seconds ($\approx$18 minutes) can be calculated in this case.

When the heating time is thus calculated, the arithmetic processing time 5 displays the sample quantity calculated in the step SP3, the heating temperature calculated in the step SP14 and the heating time calculated in the step SP15 on the display part 10, thereby relaying the processing result to the operator. After that, in the arithmetic processing part 5, the transition to the step SP16 occurs to end the procedure.

In this procedure, when the operator directs the start of a test according to the thus determined test condition, or when the operator directs the start of the test after setting the test condition with reference to the thus determined test condition by the operator, the arithmetic processing part 5 starts to heat the sample according to the test conditions depending on the operator's directions to monitor the moisture percentage, and ends the test in the lapse of the heating time. Further, the moisture percentage at the moment of this end is informed to the operator.

(2) The Operation of the Mode for Carrying Out the Invention

In the above configuration, in the moisture meter 1 (FIGS. 1 and 2), when the operator operates a key switch part 14 to input the necessary measurement accuracy, the minimum mass of the sample required for securing the measurement accuracy is calculated with reference to the measurement accuracy of mass in the moisture meter 1 determined by the processing of the load sensor 3, the analog-to-digital converter 4 and the arithmetic processing part 5 by the arithmetic processing part 5. Further, the calculation result is displayed on the display part 10. Thus, in the operator, the preliminary test and the actual test can be started by merely placing the sample of a quantity displayed on the display part 10 on the sample pan 2, so the sample quantity as one condition of the test can be set simply for that.

That is, this type of moisture meter is sometimes used for quality control, for example, and in that case, if constantly the moisture percentage is not measured in a fixed quantity of a sample, the measurement time varies, or an error is caused in the moisture percentage. Especially, such an error is remarkable in the case of controlling the change of moisture percentage for a fixed heating time.

Even if it is desirable to thus control with a fixed quantity of a sample, however, actually it is troublesome for the operator to secure the necessary measurement accuracy and determine a measurable quantity of a sample in a short time. When the calculation is simply performed on the device side by the input of required measurement accuracy to inform the required measurement accuracy to the operator as in the present mode for carrying out the invention, however, the complicated work for setting the quantity of the sample can be omitted. The quantity of the sample is a measurable sample quantity with necessary measurement accuracy kept in a short time so that the measurement result can be obtained always on the optimum conditions. Thus, the measurement condition on the sample quantity can be simply and surely set.

In the preliminary test, when the start of the preliminary test is directed by the user after the sample is placed on the sample pan 2 according to the thus informed quantity of the sample, in the moisture meter 1, heating for the sample is started at 100 degrees which is the lowest temperature enough for evaporating the moisture (FIGS. 3 and 4), and then the moisture percentage is measured in every lapse of designated time. In the moisture meter 1, when the measurement is repeated three times, the parameter p0 of the time function indicating the change of the moisture percentage is detected from the results of three times measurements.

Subsequently, the temperature is raised for a designated temperature, and similarly the parameter p1 of the time function is detected. In the moisture meter 1, the coefficients C0 and C1 of temperature functions for deriving the parameters p0 and p1 are calculated from the continuously detected parameters p0 and p1.

In the moisture meter 1, the heating temperature is again raised, and the parameter p2 of the continuous heating temperature is calculated by the similar measurement on the moisture percentage. Further, using the coefficients C0 and C1 of the temperature function calculated by the immediately preceding calculation, the parameter px in the heating temperature is calculated, and the state of heating is determined on the basis of the change of the parameter. That is, in the case of stage in which moisture is evaporated by heating, the thus actually measured parameter p2 substantially agrees with the parameter px obtained by calculation from the temperature function using the coefficient C0 and C1, and on the contrary, in the case of transition to the stage of volatilization or the like of oil in which the heating state continues, they do not agree.

Thus, in the moisture meter 1, in the case where the transition of moisture to the next stage is decided not to yet occur, the heating temperature is raised to repeat the similar procedure, and on the contrary, in the case where the transition of the heating temperature to the next stage can be decided, the immediately preceding temperature is set to the optimum heating temperature. In this procedure, the thus set heating temperature is the temperature at the stage of moisture evaporation, and the highest temperature in the temperature of moisture evaporation stage, so it is the heating temperature, which may evaporate moisture only in a short time. Thus, according to the present mode for carrying out the invention, the heating temperature as one of the measurement condition can be surely detected in a short time.

In thus detecting the heating temperature, in the moisture meter 1, a natural logarithm curve is applied to the time function. That is, in such moisture evaporation, the moisture percentage suddenly changes at the start of heating, and on the contrary, with decrease of moisture, the change of moisture percentage is gradually reduced, whereby the change of the moisture percentage can be approximated with very good accuracy by such natural logarithm curve. Also by this approximation, the measurement condition can be set with good accuracy in the present mode for carrying out the invention.

When the heating temperature is thus calculated, in the moisture meter 1, heating for the sample is discontinued to end the preliminary test. At this time, in the moisture meter 1, the heating time required for securing the measurement accuracy directed by the operator is calculated by the parameter p used in calculating the heating temperature. That is, also in such calculation of the heating time, under the condition that the measurement accuracy is secured, in order to make a measurement in a short time, the calculation has been difficult heretofore. In the present mode for carrying out the invention, however, in consideration of such measurement accuracy, the calculation is performed by effectively using the time function used in calculating the heating time, whereby the heating time as one of the measurement conditions can be obtained simply and surely.

Thus, in the moisture meter 1, the thus calculated quantity of the sample, heating temperature and heating time are displayed on the display part 10, and the operator start the measurement according to the display, whereby the moisture percentage can be simply and surely measured.

(3) Advantage of Mode for Carrying Out the Invention

According to the above constitution, the heating temperature is sequentially raised gradually to detect the parameter of the time function showing the change of the moisture percentage, and also according to the parameter, the optimum heating temperature can be calculated so as to simply and surely set the measurement condition.

That is, according to the change of the parameter of the time function, the temperature suitable for heating can be selected to simply and surely distinguish between the stage of moisture evaporation and the next stage, thereby detecting the heating temperature for completing the measurement in a short time.

Further, the parameter detected in the subsequent heating temperature is calculated by the parameter detected by the immediately preceding heating temperature, and the immediately preceding heating temperature is selected to be suitable for heating by comparison between the calculated parameter and the parameter of the measured value, whereby the highest heating temperature at the moisture evaporation stage can be selected so as to detect the heating temperature for simply completing the measurement in a short time.

The time required for heating is calculated by the parameter based on the thus obtained temperature suitable for heating, whereby the heating time of the measurement conditions can be also set simply and surely.

In the calculation for the heating time, on the basis of measurement accuracy set by the operator, the time function based on the parameter is calculated, whereby the heating time can be set to surely secure the measurement accuracy desired by the user. Therefore, the measurement condition can be simply and surely set.

The natural logarithm function is applied to the time function used in the above calculation, whereby the change of moisture percentage can be approximated with good accuracy to calculate the heating time and the like, so that the measurement condition can be simply and surely set.

Further, the required mass of the sample is calculated from the measurement accuracy set by the operator and the measurement accuracy of mass of the sample, whereby the required quantity can be simply and surely set about the mass of the sample of the measurement conditions.

(4) Another Mode for Carrying Out the Invention

Although the description of the above mode for carrying out the invention deals with the case of comparing the parameter px calculated from the coefficients C0 and C1 of the temperature function showing the parameter p with the parameter pn of observation to determine the transition of the heating stage with high accuracy, the invention is not limited to this, but in the case where practically enough accuracy can be secured, for example, in the case of simply determining the magnitude of parameter pn change to the temperature to determine the transition of the heating stage, the heating temperature may be selected according to the change of the parameter pn. Further, the heating temperature may be selected on the basis of the parameter pn.

Although the description of the above mode for carrying out the invention deals with the case of expressing the change of moisture percentage by the natural logarithm function, the invention is not limited to this, but in the case where practically enough accuracy can be secured, various time functions can be applied.

Further, although the description of the above mode for carrying out the invention deals with the case of setting the time when the dryness factor WP(t) changes up to the value for the measurement accuracy with respect to the final dryness factor WP to the end time of heating, the invention is not limited to this, but it is also considered that the final dryness factor WP is obtained by estimation. In such a case, the time function using the parameter p can be used in various ways to set the heating time to various values.

Although the above description of the mode for carrying out the invention deals with the case of informing the result of the preliminary test to the operator and accepting operator's setting, the invention is not limited to the case, but the actual measurement may be automatically according to the result of the preliminary test.

Although the above description of the mode for carrying out the invention deals with the case of using the halogen lamp as the heating source, the invention is not limited to the case, but it maybe widely applied to the cases of using various heaters as the heating source.

Although the description of the mode for carrying out the invention deals with the case of applying the invention to the moisture meter, the invention is not limited to the case, but in some case, the moisture meter is controlled and used by a computer as an external device, so it may be widely applied to such a case. In the case, the whole or apart of the processing in the arithmetic processing part related to the above mode for carrying out the invention is performed by the computer as an external device.

Further, the automatic determination of heating temperature is described as follows.

Figure 7:
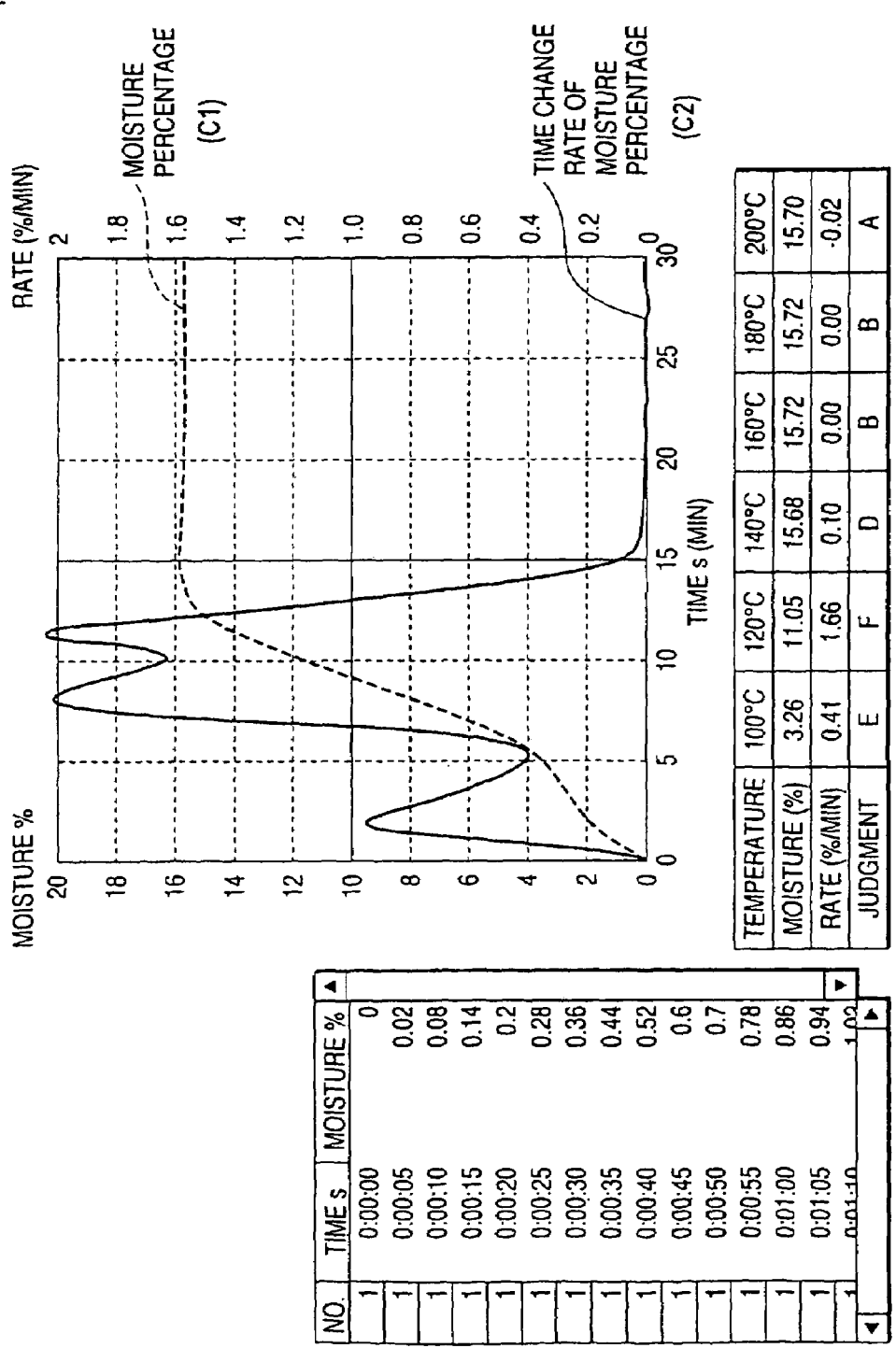
FIG. 7 shows an example of measuring potassium sodium dihydrate as a sample with RsTemp.

FIG. 7 shows an example of measuring potassium sodium dihydrate as a sample with RsTemp. (Re Temp is "Heating Temperature Determination Software" adapted to automatically determine a suitable heating temperature in measuring the moisture percentage of a sample using A & D heating dry type moisture meters MX-50, MF-50.)

The elapsed time enters the horizontal axis, and the moisture percentage is measured with the heating temperature automatically raised at five-minute intervals at space of 20° C., i.e. at the heating temperature of 100° C. for 0 to 5 minutes from the start of measurement, at 120° C. for 5 to 10 minutes, at 140° C. for 10 to 15 minutes, at 160° C. for 15 to 20 minutes, at 180° C. for 20 to 25 minutes, and at 200° C. for 25 to 30 minutes.

A curve C1 in the graph is a change of moisture percentage, the numerical value of which enters the left vertical axis. It is known that its gradient (inclination) varies with the change of the heating temperature.

A curve C2 in the graph is obtained by plotting the gradient (%/min) per minute of the moisture percentage change curve (C1), and its numerical value enters the right vertical axis. In other words, when the moisture percentage is taken as M(t), the moisture percentage curve (C1) (function) is linearly differentiated by the time t to obtain a curve (function) dM(t)/dt which is the curve C2. (The temperature T is constant in each heating temperature section.)

The thus measured and calculated results are shown in a table below the graph. In the table, from the upper side first, Temperature: Heating Preset Temperature, which is automatically set.

Moisture (%): Moisture Percentage

Rate (%/min): Change Amount of Moisture Percentage per Minute

Judgment: The determination result on the heating temperature suitable for measuring the moisture percentage, and it is determined in alphabetical order of A, B, C, D, E, and F. The heating temperature of the determination A is determined to be the heating temperature optimum for measuring the moisture percentage of this sample.

The determination on the heating temperature is performed by evaluating the stability of moisture percentage (gradient of a moisture percentage curve or linear differentiated value Rate (%/min) at the respective temperatures from the results of measurements at various heating temperature.

ReTemp determines the heating temperature suitable for the sample from the measured and calculated results, and it is the important thing in deciding the heating temperature of the sample that in addition to this, the progress of the sample state is observed by visual observation and the sense of smell of a test and research person, that is, the properties of the sample such as melting, burning, smelling and decomposing are observed to finally decide the optimum heating temperature including the above.

Some examples of heating temperature determination will now be shown with the Rs Temp.

Figure 8:
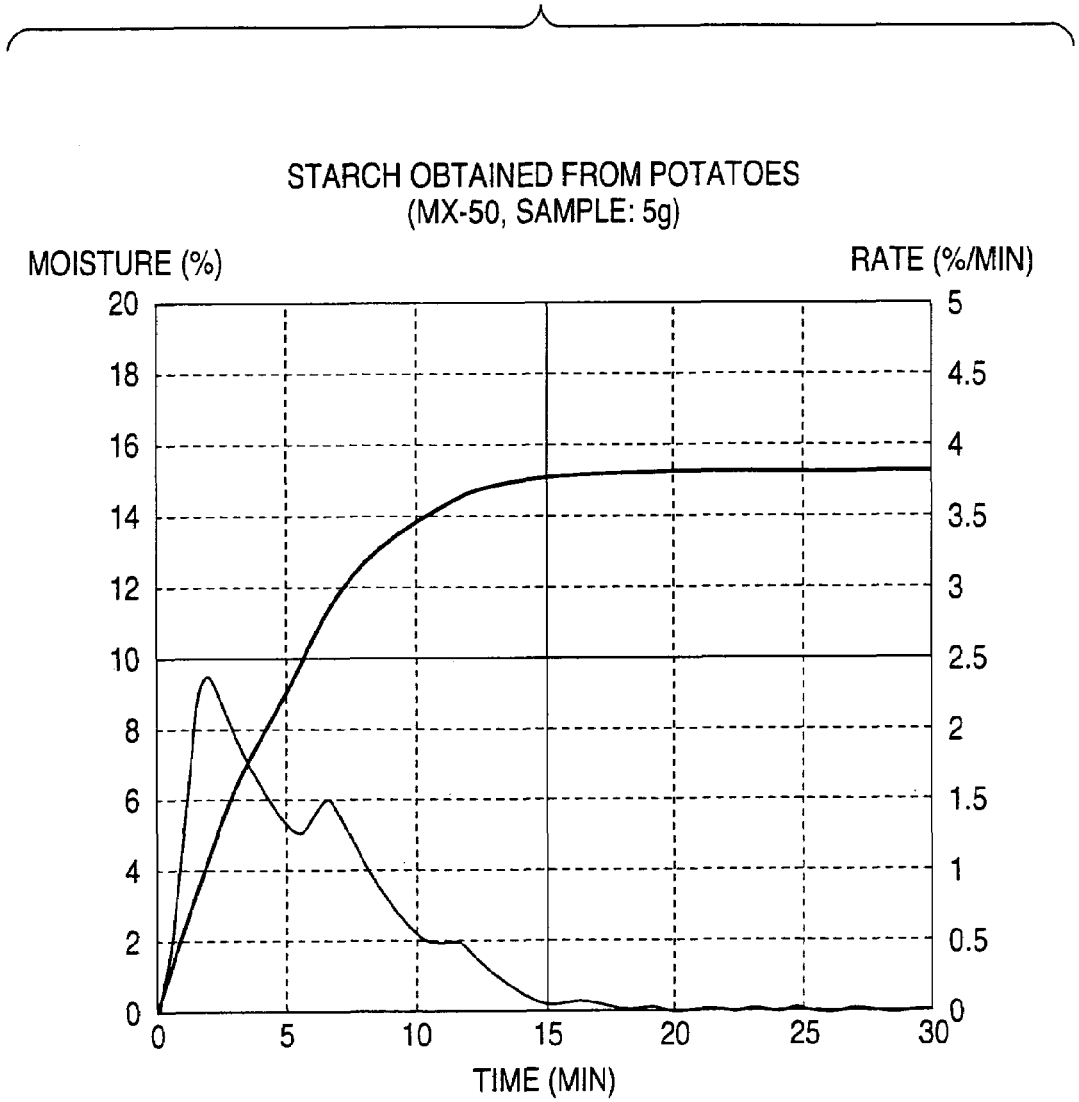
FIG. 8 shows the measurement result of starch obtained from potatoes.
Figure 9:
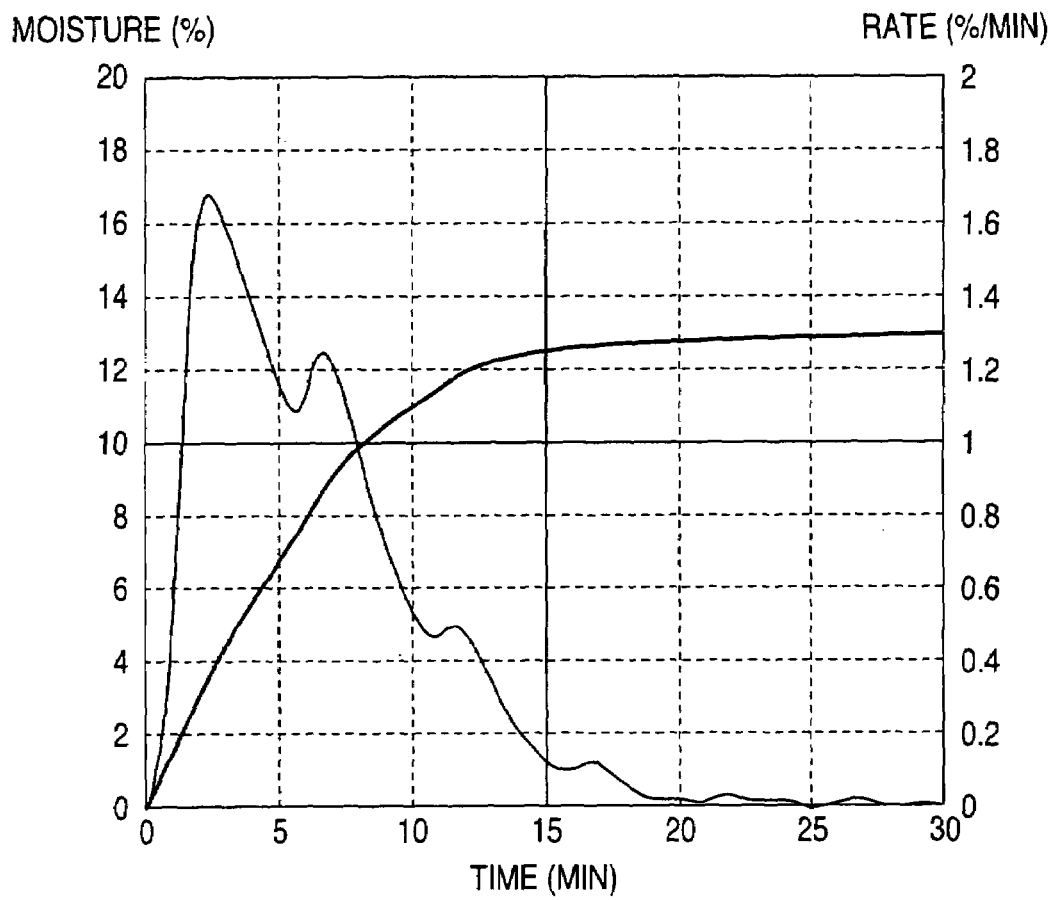
FIG. 9 shows the measurement result of cornstarch.

1. Measurement Example in Which the Heat Resisting Temperature of a Sample is High and Even if the Heating Temperature is Changed, the Finally Obtained Moisture Percentage is Substantially Constant FIG. 8 shows the measurement result of starch obtained from potatoes, and FIG. 9 shows that of cornstarch. It is known that the rate (%/min) stably shows a low value in a high temperature region.

The measurement on this type of sample can be ended in a short time by measuring the sample at the heating temperature as high as possible.

In addition to FIG. 9, potassium sodium dihydrate in the above example, hand soap, washing starch, soft wheat flour, milk (vegetable oil), agar powder and the like will make such a measurement progress.

Figure 10:
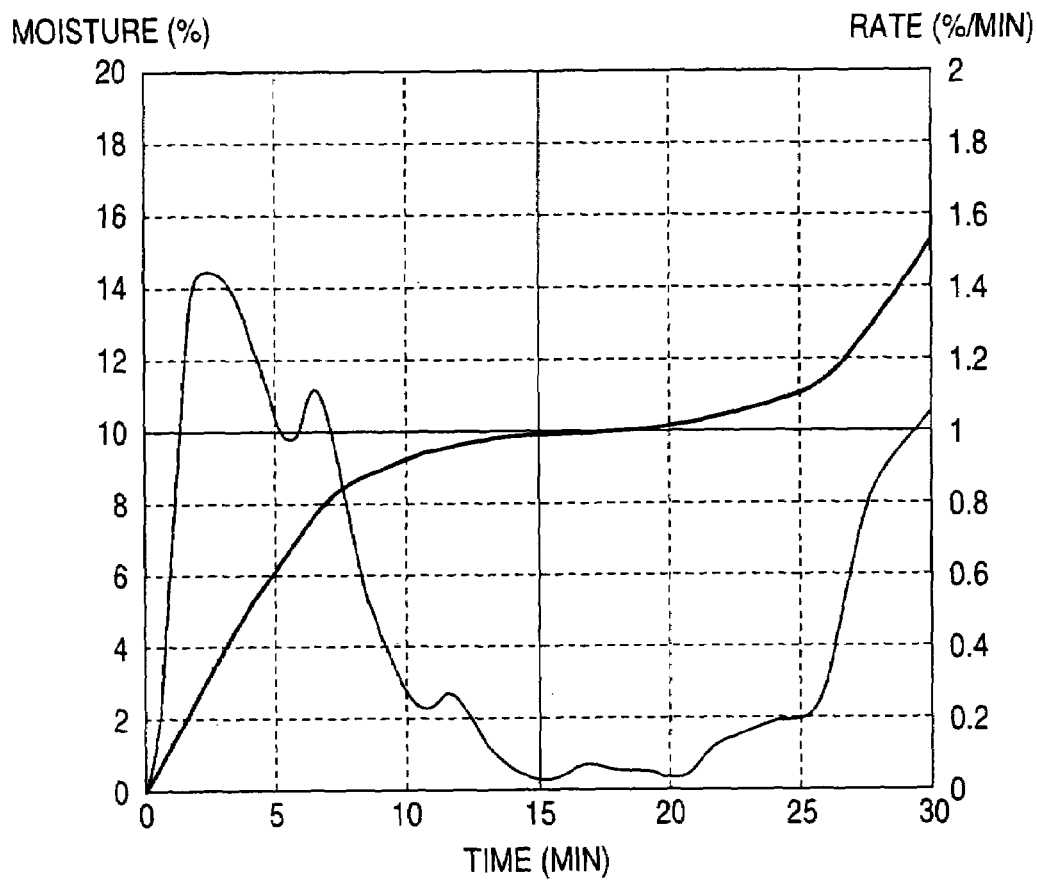
FIG. 10 shows the measurement result of soybean powder as a sample.
Figure 11:
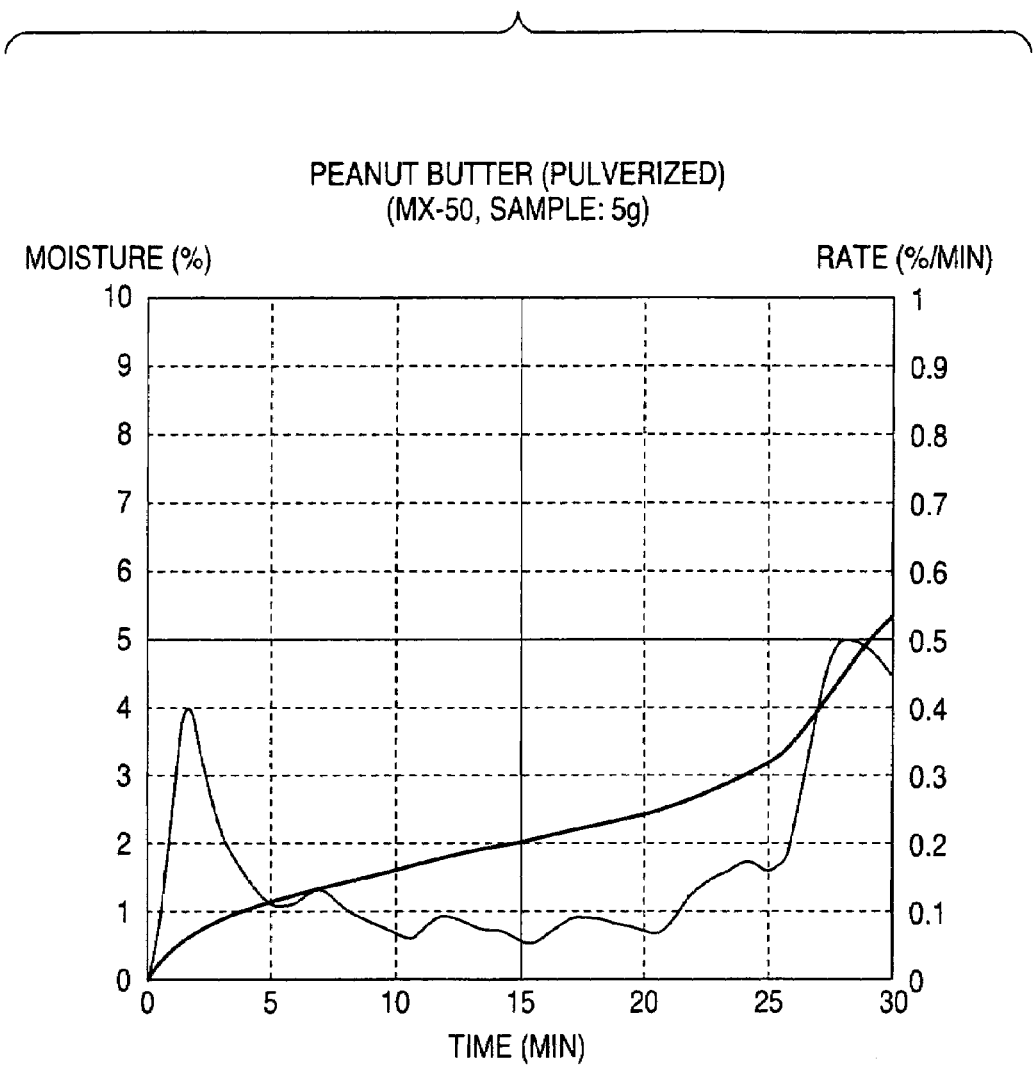
FIG. 11 shows the measurement result of peanut butter.

2. Measurement Example in Which When the Heating Temperature Becomes High, the Gradient (Inclination) of a Moisture Percentage Measurement Curve Suddenly Increases at a Certain Temperature and Higher FIG. 10 shows the measurement result of soybean powder as a sample, and FIG. 11 shows that of peanut butter.

From the start of measurement, the rate (%/min) tends to rise and fall, and it once shows a low value and again starts to rise. It is considered that the reason why it again starts to rise at the heating temperature equal to or higher than 180° C. is that ingredients other than moisture (lipid, organic matter, an additive) start to transpire, and carbonization of the sample starts.

In the case of this type of sample, when the heating temperature is too high, sometimes the reliability, reproducibility and accuracy of measured values are lowered.

It is preferable that the moisture percentage is measured at the heating temperature before the rate (%/min) starts to rise again.

According to the invention, as described above, the heating temperature is sequentially raised gradually to detect the parameter of the time function showing the change of moisture percentage, and the optimum heating temperature is calculated on the basis of the parameter, or the required mass of the sample is calculated from the measurement accuracy set by the operator or the measurement accuracy of the mass, whereby the measurement condition can be set simply and surely.

What is claimed is:

1. A control method for a moisture meter, comprising:
   heating a sample by sequentially raising a heating temperature to detect a time rate of change of moisture percentage for the sample, said time rate of change of moisture percentage being detected by measuring a change of mass of the sample during heating;
   detecting at least one value of a pre-determined parameter of a time function related to said time rate of change of moisture percentage; and
   determining and selecting an optimum heating temperature for the sample in accordance with the detected value of said parameter by determining a first value of the parameter at a subsequent heating temperature using a second value of the parameter at an immediately preceding heating temperature, comparing the first and second values, and in response to the comparison, determining and selecting the immediately preceding heating temperature as the optimum heating temperature.

2. The method of claim 1, wherein said determining includes determining and selecting the optimum heating temperature in accordance with a change in value of the parameter from the step of sequentially raising of the heat temperature.

3. The method of claim 1, further comprising:
   determining an optimum heating time for the sample in accordance with time lapsed to reach said optimum heating temperature.

4. The method of claim 3, wherein the step of determining the optimum heating time includes determining a time rate of change of the parameter value in accordance with an accuracy threshold for the moisture percentage set by a user.

5. The method of claim 4, wherein the step of determining the optimum heating time includes determining said time rate of change of the parameter value of the time function wherein said time function is associated with a natural logarithmic function.

6. The method of claim 1, wherein the step of heating includes heating the sample and measuring the change in mass of the sample in accordance with an accuracy threshold for the mass of the sample set by a user.

7. The method of claim 1, further comprising:
   displaying the determined optimum heating temperature to a user.

8. A machine-readable medium having stored thereon a plurality of executable instructions, the plurality of instructions comprising instructions to:
   heat a sample by sequentially raising a heating temperature to detect a time rate of change of moisture percentage for the sample, said time rate of change of moisture percentage being detected by measuring a change of mass of the sample during heating;
   detect at least one value of a pre-determined parameter of a time function related to said time rate of change of moisture percentage; and determine and select an optimum heating temperature for the sample in accordance with the detected value of said parameter.

9. The medium of claim 8, further comprising instructions to:
display the determined optimum heating temperature to a user.

10. A moisture meter, comprising:
a controller for heating a sample by sequentially raising a heating temperature to detect a time rate of change of moisture percentage for the sample, said time rate of change of moisture percentage being detected by measuring a change of mass of the sample during heating using a load sensor and an analog-to-digital converter;
said controller detecting at least one value of a predetermined parameter of a time function related to said time rate of change of moisture percentage, and determining and selecting an optimum heating temperature, using a temperature sensor, for the sample in accordance with the detected value of said parameter.

11. The moisture meter of claim 10, further comprising:
a display for displaying the determined optimum heating temperature to a user.

* * * * *